United States Patent [19]

Ellestad

[11] 4,256,101
[45] Mar. 17, 1981

[54] THERMISTOR ASSIST SENSING

[75] Inventor: Raymond A. Ellestad, Rialto, Calif.

[73] Assignee: Bourns Medical Systems, Inc., Riverside, Calif.

[21] Appl. No.: 17,792

[22] Filed: Mar. 5, 1979

[51] Int. Cl.³ ............................................ A61M 16/00
[52] U.S. Cl. ............................ 128/204.23; 128/204.26
[58] Field of Search ............... 128/145.5, 145.6, 145.8, 128/724, 204.21, 204.22, 204.23, 204.26; 73/204; 340/606

[56] References Cited

U.S. PATENT DOCUMENTS

| | | | |
|---|---|---|---|
| 3,952,739 | 4/1976 | Cibulka | 128/204.23 |
| 3,962,917 | 6/1976 | Terada | 128/724 |
| 3,972,327 | 8/1976 | Ernst et al. | 128/145.8 |
| 4,043,196 | 8/1977 | Trageser | 73/204 |
| 4,106,503 | 8/1978 | Rosenthal et al. | 128/145.6 |
| 4,141,356 | 2/1979 | Smargiassi | 128/145.8 |

FOREIGN PATENT DOCUMENTS

| | | | |
|---|---|---|---|
| 2317431 | 10/1974 | Fed. Rep. of Germany | 128/724 |
| 584845 | 12/1977 | U.S.S.R. | 128/724 |

Primary Examiner—Henry J. Recla
Attorney, Agent, or Firm—William G. Becker

[57] ABSTRACT

A sensor for the detection of a very feeble effort to breathe on the part of a patient whose breathing needs are under the influence and control of a mechanical ventilator. A self-heated thermistor is mounted in a small diameter sensor tube. A diaphragm and chamber arrangement limits the volume of air that flows in the sensor tube past the self-heated thermistor. The self-heated thermistor is mounted in the center of the small diameter sensor tube so that a low volume flow rate of fluid will cause a relatively large amount of cooling. Thus a very small effort to breathe will draw a limited volume of fluid past the thermistor at a high velocity, causing rapid cooling. A voltage change resulting across the thermistor is utilized to signal a patient effort to breathe and to command the ventilator to furnish an assisted breath where appropriate.

12 Claims, 4 Drawing Figures

THERMISTOR ASSIST SENSING

CROSS REFERENCE TO RELATED APPLICATION

Specific reference to Applicant's related patent application, filed concurrently herewith, and assigned to the same assignee, for "Directional Thermistor Assist Sensing", Ser. No. 17,793 is hereby given.

BACKGROUND OF THE INVENTION

1. Field of the Invention

This invention relates generally to mechanical ventilators and respiratory aids and more particularly to patient effort sensing means whereby the ventilator may be commanded to an appropriate operating mode.

2. Description of the Prior Art

While presently available respiratory systems can furnish operating modes of various parameter bases, it becomes important with very weak patients to sense an almost infinitesimal attempt to breathe. On the other hand, excessive pandering to the respiratory needs of the patient can build up a harmful addiction of the patient upon the ventilator such that the patient will be unable to breathe on his own even after he has physically recovered sufficiently so to do.

Modern respirators, therefore, have been developed in response to patient need, and may thus operate in a number of modes among which are commonly included a control mode. In the control mode, a patient is totally dependent on the ventilator for his respiratory needs. That is to say, the ventilator completely controls all the respiratory functions of the patient including rate of breathing, volume of breathing gas to be inhaled by the patient, and all other rates and pressures permitted to and furnished by the ventilator to the patient.

In another mode, the assist mode, in response to an initial effort by the patient to breathe, the ventilator "assists" the patient by delivering a predetermined breath to the patient. The breath so delivered is in all ways similar to the above-described controlled breath except that the rate of breathing is determined by the patient himself in response to his efforts to breathe. In the pure assist mode, therefore, no breath is furnished to the patient until he makes an effort to breathe on his own. Stated in another way, if the patient does not attempt to breathe on his own, no breath will be furnished to him by the machine. It is thus of the utmost importance that every effort, no matter how feeble, that the patient makes no breathe be sensed. If the effort is not sensed, then no breath can be furnished to the patient as a result of this effort and he remains dependent upon the backup provisions, if any, of the ventilator. Thus his dependence upon the machine would become increased and his addiction thereto exacerbated.

Another mode of lesser interest in the instant invention is denominated the spontaneous mode. In the spontaneous mode the ventilator functions primarily to furnish blended breathing gas to the patient as required by him by maintaining a constant positive airway pressure (CPAP). In this mode, the patient must be strong enough to draw sufficient breathing gas into his body to constitute a complete breath. In the ventilator machine to be described as an exemplar for the purpose of explaining the instant invention, the spontaneous mode will have little, if any, application.

Although some prior art respirators have been satisfactory in their operation to a point, it has been found that they were lacking in sensitivity in some respects. The needs of some patients were thus not met under some conditions. For example, one patient may be able to initiate a stronger breathing impulse than another. If the weaker patient's effort is not also sensed, however, the purpose of the assist mode is not being implemented in his case. It thus becomes important to mechanize as sensitive a system as possible in order to sense every effort, no matter how feeble, on the part of a respirator patient to breathe.

Many different schemes have been employed in attempts to solve the respirator problems presented. Most have either presented new problems or only partially solved the problems presented, or both. Most of these devices have thus met special needs as presented by specific problems and have, therefore, served narrow purposes. These prior art devices, among other disadvantages, have been unreliable and unpredictable in operation under continued use and have been expensive and complicated to manufacture. Some of these prior art devices have been described in the following listed patents that were brought to the attention of the applicant through a novelty search conducted in the United States Patent and Trademark Office:

| U.S. Pat. No. | Title | Patentee |
| --- | --- | --- |
| 3,903,876 | Respiration Monitor | T. R. Harris |
| 3,645,133 | Electronic Spirometer | P. G. Simeth |
| 3,438,254 | Fluid Flow Detector | E. B. Seeley |
| 3,368,212 | Gas Flow Monitor | S. D. Klyce |
| 3,316,902 | Monitoring System for Respiratory Devices | H. T. Winchel |
| 3,085,431 | Flow Measuring Apparatus | A. J. Yerman |

Upon examination of the above listed patents, the following analyses were made by Applicant and are submitted herewith for the convenience of the Examiner.

With respect to the Respiration Monitor, U.S. Pat. No. 3,903,876, to Harris, it is observed that this device would not be suited for use with a ventilator because it is not intended for use in closed system. The tubes are open to the atmosphere at several points including right at the patient, which construction will not operate satisfactorily with a positive pressure ventilator. The device has three additional disadvantages, among others, when compared with Applicant's invention. First, this device is designed to sense flow irrespective of direction. It is thus possible that an extra breath could be delivered when the patient needs to exhale rather than to inhale. Second, because all directional flow is sensed, there may be less dead time in which the thermistor can recover. And third, it is felt that it would be impossible to achieve the sensitivity that has been achieved with Applicant's invention.

With respect to the Electronic Spirometer, U.S. Pat. No. 3,645,133, to Simeth et al, it is observed that this device places a thermistor in line to measure patient flow with a second thermistor placed separately for temperature compensation. Since the thermistor is located in the main line, the cross-section at that point must be sized for full patient flow. The result is that a relatively large volume of air must move past the thermistor which means poor sensitivity and poor response time in comparison with Applicant's invention.

With respect to the Fluid Flow Detector, U.S. Pat. No. 3,438,254, to E. B. Seeley, it is noted that this device is also a main line sensing system subject to the disadvantages mentioned above. It also appears that this method is more complex and bulky than Applicant's invention.

With respect to the Gas Flow Monitor, U.S. Pat. No. 3,368,212, to S. D. Klyce, it is noted that a pressure differential between patient system and atmosphere caused by patient flow is relied on to cause airflow through a tube to cool a thermistor. Since the device described herein does not use a closed system, it would not be suitable for use with a positive pressure ventilator.

The greatest part of the patent to H. T. Winchel et al for a Monitoring System for Respiratory Devices, U.S. Pat. No. 3,316,902, deals with the circuitry and basic principles of breath rate monitors and patient assist function. The thermistor probe in this device is mounted directly to the body of the patient. There are several problems with this approach. Among them: (1) There is a shock hazard involved whenever an electrical device is mounted directly to a patient. If the thermistor were insulated sufficiently well to prevent all danger, the sensitivity or response time would be adversely affected. (2) At the patient, there is a great deal of humidity, mucus, and miscellaneous foreign matter which could accumulate on the thermistor and thus affect its performance. (3) Anything outside the ventilator which must be handled by therapists, nurses, and other personnel is subject to abuse and breakage. (4) If the thermistor is in contact with the patient, it needs to have provisions for disconnecting it from the ventilator to sterilize it. It must also be able to withstand sterilizing temperatures. It is felt that these disadvantages weigh very heavily against the device of this patent in respect of Applicant's invention.

Another interesting patent brought to Applicant's attention is the Flow Measuring Apparatus, U.S. Pat. No. 3,085,431 to A. J. Yerman et al. One major disadvantage of the device described in its complexity. It is designed for accurate measurement rather than merely to sense an attempted initiation of flow.

It would thus be a great advantage to the art to provide a system of greater sensitivity to patient effort than that presently available.

SUMMARY OF THE INVENTION

In view of the above stated problems associated with the prior art, an object of the present invention is the provision of a more sensitive means of sensing patient breathing effort than is presently available.

Another object of the present invention is the provision of the above more sensitive means in a form such as may be utilized to modify existing systems.

A further object of the present invention is the provision of the above means in an economical and convenient package so as to modify existing systems.

The device of the invention provides a sensing mechanism that utilizes a thermistor associated with a sensitive diaphragm, a chamber and a small diameter tube arranged to cause a large velocity of fluid flow past the thermistor to provide maximum cooling so as to increase sensitivity to a patient's effort to breathe as hereinafter described.

BRIEF DESCRIPTION OF THE DRAWINGS

Further advantages and features of the present invention will be more fully apparent to those skilled in the art to which the invention pertains from the ensuing detailed description thereof, regarded in conjunction with the accompanying drawings, wherein like reference characters refer to like parts throughout and in which.

DETAILED DESCRIPTION

Although specific embodiment of the invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are deemed to be within the spirit, scope and contemplation of the invention as further defined in the appended claims.

Figure 1:
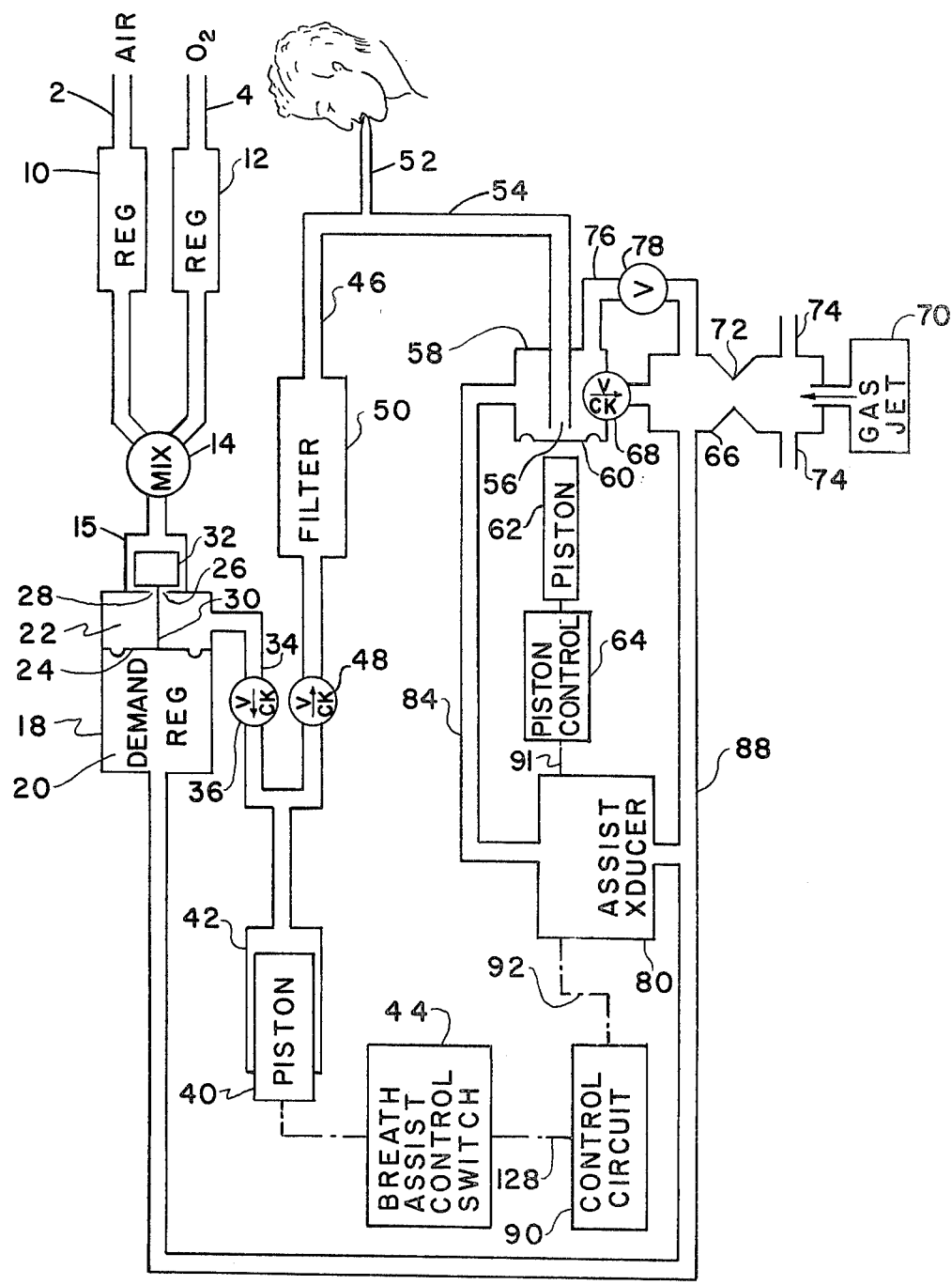
FIG. 1 is an idealized conceptual block flow diagram illustrating the general characteristics of a modern ventilator.

Referring to FIG. 1 with greater particularity, a generalized flow diagram illustrating the characteristics of a modern ventilator is presented. Air is received in an air inlet 2 and fed through regulator 10 into mixing valve 14. Oxygen, likewise, is received in an oxygen inlet 4 and fed through oxygen regulator 12 to the same mixing valve 14. After being mixed in mixing valve 14, the air/oxygen mixture is received in inlet chamber 15 of a demand regulator 18 which is further divided into a reference chamber 20 and a sensing chamber 22, the last two chambers being separated by a flexible, resilient diaphragm 24. Inlet chamber 15 and sensing chamber 22 are separated by a wall 26 having a central opening 28 through which a rod 30 extends from the diaphragm 24 to the interior of chamber 15. A stopper 32, affixed to the end of rod 30 within chamber 15, normally abuts the dividing wall 26 to cover opening 28, thereby preventing any flow of air between chambers 15 and 22. This flow restriction is removed when the gas pressure in chamber 22 is reduced by a predetermined amount while the gas pressure in chamber 20 remains at a constant level. In this event, diaphragm 24 flexes into the area formally occupied by chamber 22 (to the right in FIG. 1), moving stopper 32 out of contact with the dividing wall 26 and allowing the gas mixture to flow from air and oxygen supplies into air and oxygen inlets 2 and 4, respectively, through regulators 10 and 12, into and through mixing valve 14 and chamber 15 into chamber 22. The demand regulator 18 thus functions much as a scuba tank regulator in which a pressure drop is produced when the user attempts to inhale, opening up a line from an air supply.

Sensing chamber 22 is connected via a conduit 34 and check valve 36 to a breath assist mechanism which includes a piston 40 slidably lodged within a cylinder 42. A breath assist control switch 44 governs the operation of the breath assist mechanism. A negative pressure is created in sensing chamber 22 when piston 40 is drawn backward (to the left in FIG. 1), thus flexing the diaphragm 24 and thereby uncovering opening 28 to enable an air-flow from air and oxygen supplies through regulators 10 and 12, into and through mixing valve 14, through chamber 22, conduit 34 and check valve 36 into cylinder 42 as long as piston 40 continues to move backward. Breath assist control switch 44 actuates the breath assist mechanism when commanded by signalling piston 40 to drive forward, thus charging the air mixture in cylinder 42 into the patient supply conduit 46 by way of check valve 48 and filter 50. The volume of gas delivered to the patient may be either a preset amount, or determined dynamically by providing well-known apparatus to measure the patient's lung pressure and terminate forward movement of piston 40 when lung pressure reaches a desired level.

A patient supply conduit 46 provides a gas conduit between the breath assist apparatus and the patient. The conduit system includes a check valve 48 which prevents a backflow of exhaled gas from the patient to the breathing air sources, and a filter and/or humidifying device 50 to treat the breathing air before delivery to the patient. An endotracheal tube 52 may be fitted to the conduit system in a tee connection to conduct air to and from the patient.

The conduit system further includes an outlet or expiratory branch 54 having an outlet port 56 enclosed within a variable pressure chamber 58, one wall of which forms a diaphragm 60 in registry with outlet port 56. A piston 62 is located to alternately flex the diaphragm 60 to a position blocking the outlet port 56 when the piston is in a forward position, and to release the diaphragm 60 and allow gas to flow out of the conduit system 54 through outlet port 56 when the piston 62 is in a retracted position. A piston control device 64 such as a solenoid under the control of an assist transducer 80 and control circuit 90 causes the piston 62 to block the outlet port 56 during inspiration and uncover the port during expiration.

While the patient's breathing behavior may be sensed in a number of ways, such as by measuring the pressure within the conduit system 46 and actuating the breath assist mechanism whenever the pressure falls below a particular level, the present invention contemplates a unique and ultrasensitive method to be explained subsequently.

In the conventional ventilator, chamber 58 communicates with a second chamber 66 through a check valve 68 that permits a gas flow only from chamber 58 into chamber 66. The pressure within chamber 66 is positively maintained at a constant level by means of a gas jet source 70 that delivers a steady jet stream through a venturi 72 and into the chamber 66. A number of outlet orifices 74 are located between gas jet source 70 and venturi 72 to allow gas exhaled by the patient to exit from the respirator system. Gas jet source 70 is adjustable within a range that permits the pressure inside chamber 66 to be set between zero and 15 centimeters of water gage (zero to approximately 0.2 pounds per square inch gage). A bleeder conduit 76 enables a backflow of gas from chamber 66 to enter chamber 58, with an adjustable needle valve 78 forming a restriction in the line to limit the flow rate (gas flowing in the opposite direction, from chamber 58 to chamber 66, is transmitted through check valve 68). Needle valve 78 may be adjusted from a full open position, at which the gas flow through the bleeder conduit 76 is substantially unrestricted, to a completely closed position.

Dynamic control of the breath assist mechanism starts at assist transducer 80. A pressure differential between PEEP reference conduit 88 and connecting tube 84 must be sensed therein. The acronym PEEP denotes positive expiratory end pressure. PEEP pressure is incident also at PEEP reference chamber 20. Assist transducer 80 develops signal information useful to control piston control device 64 by way of signal line 91 and breath assist control circuit 90 by way of signal line 92. Breath assist control switch 44 is responsive to signal transmitted by way of signal line 128 from control circuit 90 and thereby controls piston movement in piston cylinder 42. As is evident from the foregoing discussion, the sensitivity of the total ventilator system is dependent upon the sensitivity of assist transducer 80. Therefore, in order to develop a more sensitive system, one of the most important elements is the sensitivity of assist transducer 80. It is to this component in the overall ventilator system that Applicant's invention is primarily directed.

Figure 2:
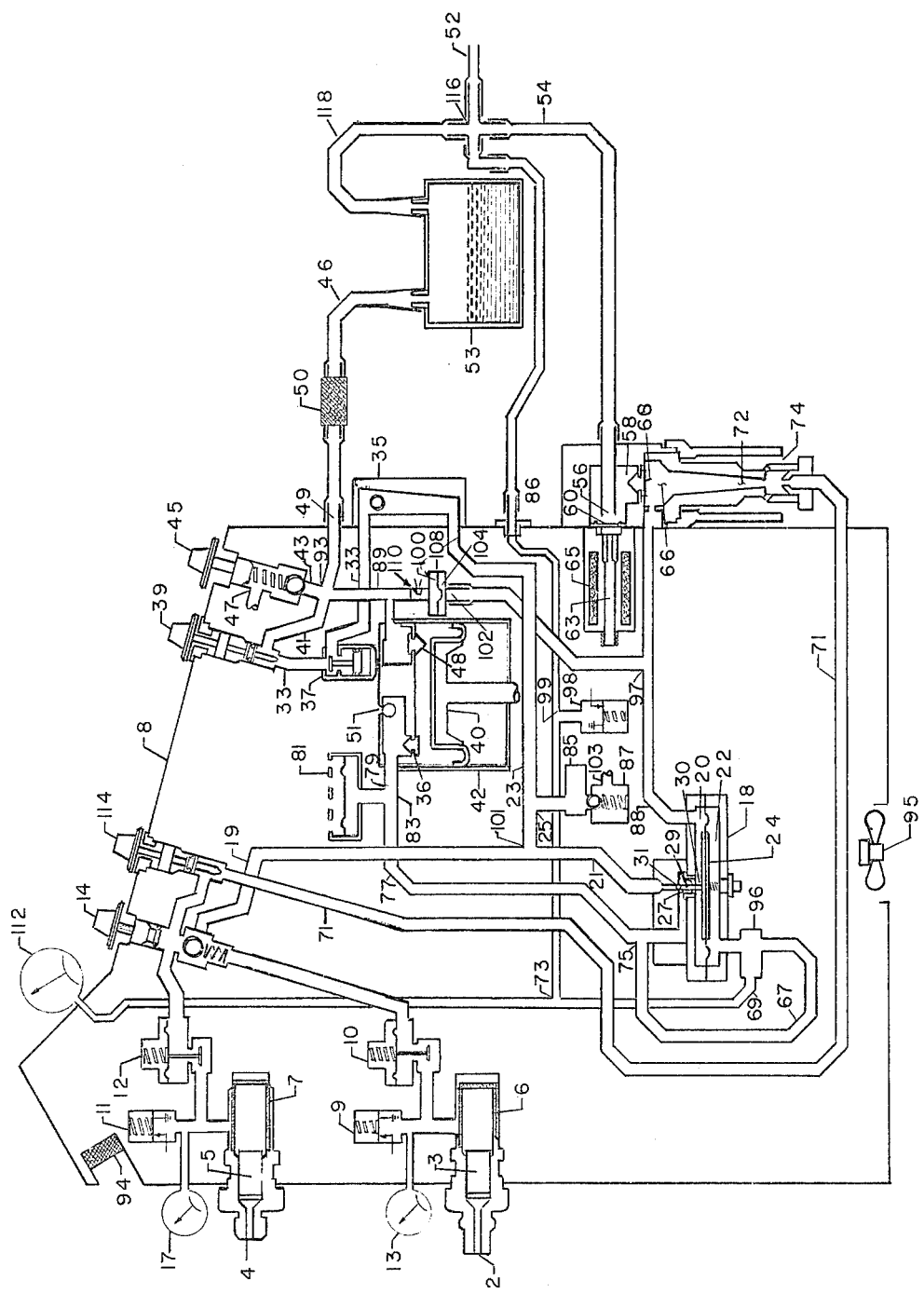
FIG. 2 is a combined perspective and flow schematic of a ventilator showing incorporation of Applicant's inventive device therein.

In FIG. 2, there is illustrated a system in which the sensing transducer as contemplated by Applicant's invention has been incorporated. As in FIG. 1, air and oxygen inlets are denoted respectively by numerals 2 and 4. The air accepted by the system and incident at mixing valve 14 has been processed through air check valve 3, air filter 6, air pressure alarm switch 9 and air regulator 10. An air inlet pressure gage 13 monitors the incident air pressure. In like manner, the oxygen incident at mixing valve 14, after having been accepted by the machine through oxygen inlet 4 and led through oxygen check valve 5 and oxygen filter 7 is incident upon oxygen pressure alarm switch 11 and regulated by oxygen regulator 12. Again, an oxygen inlet pressure gage is denoted by the numeral 17. When the apparatus is mounted in a cabinet as indicated in this FIG. 2, it is necessary to have cooling air. Therefore, a cooling air intake is identified by the numeral 94 while the cooling air exhaust fan is identified by the numeral 95. The control console and cabinet have been assigned the identifying numeral 8. The PEEP reference pressure system comprises the constant pressure chamber 66, PEEP venturi 72 and outlet orifices 74 with a gas jet supply conduit 71. This pressure is incident at PEEP control valve 114. The breathing gas as blended in mixing valve 14 is fed through a conduit 19 by way of a tee 101 into conduit 23 and through flowmeter 35 through safety valve 37 and conduit 33 to flow control valve 39. Flow control valve 39 supplies the blended gas by way of conduit 41 through cross coupling 93 into filter 50 thence through patient supply conduit 46 to a humidifier 53. After being humidified, the breathing gas is then supplied through conduit 118 to cross connector 116 and finally to endotracheal tube 52 to the patient. As may be easily seen, there are many auxiliary circuits and safety devices included. For example, a part of the piston system, comprising the piston 40 and piston cylinder 42, has to do with a safety valve 50 and a compliance chamber 81. Upon rapid retraction of piston 42, compliance chamber 81 prevents outside air from contaminating the system. As is seen, compliance chamber 81 is in fluid communication with piston cylinder 42 by means of a tee 79 and a conduit 83. A check valve 36 allows breathing gas to be charged into cylinder 42. Another check valve 48 allows breathing gas to be supplied from cylinder 42 into the patient supply conduit.

It is interesting to trace another fluid path followed by the air/oxygen mixture. A tee 25 permits the pressure of the air/oxygen mixture in conduit 19 to influence a bleed solenoid 85 that controls a vent 103 by means of bleed valve 87. This bleed system is instrumental in maintaining desired gas mixtures under certain minimum flow conditions, however, when the system is not in use, the bleed valve should be closed in order to conserve gas. The bleed solenoid 85 performs the function of shutoff for the valve 87.

Tee 101 supplies the air/oxygen mixture to demand regulator 18. Demand regulator 18 comprises an opening 27 directly in fluid communication with conduit 19 by means of tee 101 and conduit 21; a ball seal 31; a valve seat 29; a rod 30 attached to a diaphragm 24; and PEEP and reference sensing chambers 20 and 22, respectively. The operation of demand regulator 18 is effected by means of the interrelationships between demand solenoid 96 and its interconnections by means of conduits 67, 69 and tees 73 and 75. Such connections and relationships are common in the art and are important in the instant case only insofar as an overall system is rendered more understandable by such exposition.

Expiratory conduit 54, as explained with reference to FIG. 1, connects to variable pressure chamber 58 which contains outlet port 56 which is in turn controlled by diaphragm 60 under the action of armature 63 which is activated by exhalation solenoid 65. The constant pressure reference chamber, as noted above, is identified by the numeral 66, while the expiratory check valve permitting only one way fluid communication from variable pressure chamber 58 to constant pressure reference chamber 66 is denoted by the numeral 68.

The constant reference pressure developed in chamber 66 is the PEEP reference pressure for the system as set and controlled by PEEP control valve 114 and this reference pressure is incident in the PEEP reference chamber of demand regulator 18 by means of conduit 88. A tee connection 97 in conduit 88 furnishes PEEP reference pressure to thermistor sensing probe 100. Thermistor sensing probe 100 comprises a reference tube 102 for receiving PEEP reference pressure; a chamber 104; a diaphragm 108 isolating chamber 104 from PEEP reference pressure; a sensing tube 106 (FIG. 3) and a thermistor 110. This assembly is connected by means of a tee to the piston cylinder 42 and by means of conduit 89 to the patient supply conduit 49. A pressure relief valve 45 is connected by means of a tee 43 into cross coupling 93 and permits venting of any excess pressure developed in this conduit line to atmosphere by way of vent 47.

An additional auxiliary fluid circuit is provided by the proximal airway conduit 86 connected to cross connector 116. Proximal airway conduit 86 is connected to pressure transducer 98 by a tee 99 and to proximal airway pressure gage 112 and demand solenoid 96 by means of tee 73.

The operation of compliance chamber 81 ensures that the breathing gas supplied to the patient does not become contaminated by way of safety valve 51. For example, under the condition that piston 40 begins to retract rapidly, a negative pressure, great enough to open safety valve 51 may be developed. In that event, room air could be sucked in through check valve 36 and upset the air/oxygen balance intended to be furnished to the patient as charged into cylinder 42. However, since the compliance chamber 81 is in the system, its diaphragm will deflect and allow gas to flow from the capacity of the compliance chamber itself very easily into the piston cylinder 42, thus allowing demand valve 18 time in which to open completely and thus furnish the desired air/oxygen mixture through conduit 77 into the cylinder 42. It is easily determined that the overall system here presented can be no more sensitive than the thermistor sensing probe 100 which senses a feeble effort to breathe by a patient, as will be explained with reference to FIG. 3.

Figure 3:
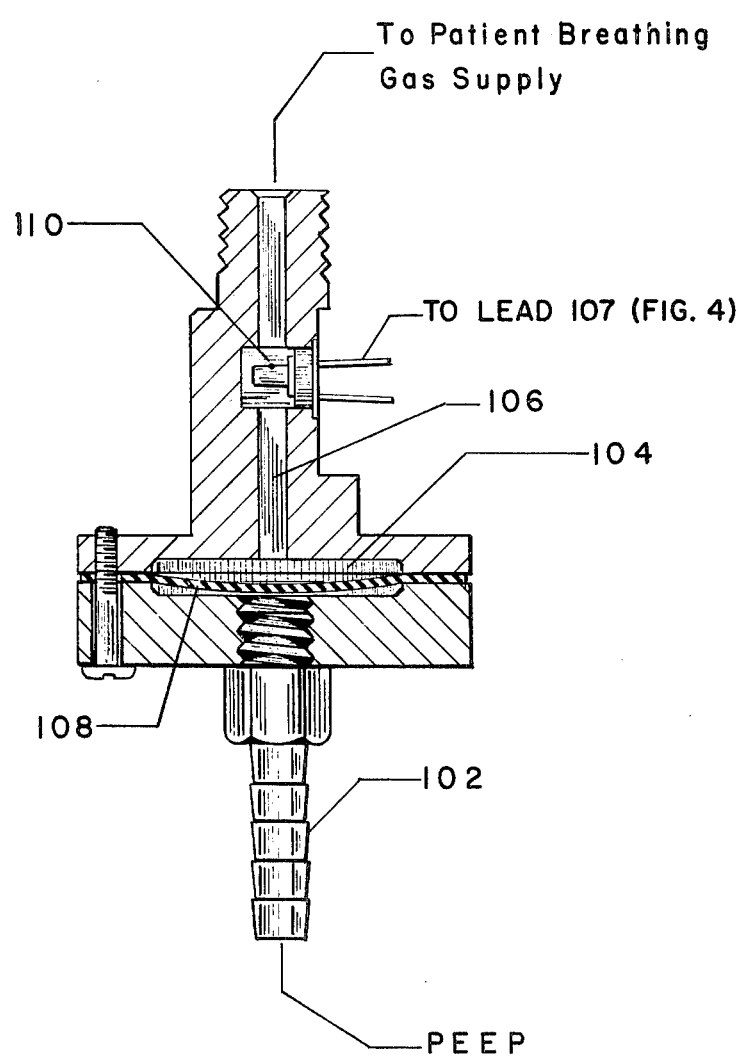
FIG. 3 is a detailed perspective in cross-section of the thermistor sensing probe of the invention.

Referring now more particularly to FIG. 3, the thermistor sensing probe is shown in detailed cross-section. At the bottom of the figure, reference tube 102 transmits the influence of PEEP reference pressure to diaphragm 108 situated in chamber 104. Sensing tube 106 contains thermistor 110 between chamber 104 and conduit 89 that supplies the patient breathing gas. With reference once more to FIG. 2, it may be seen that a patient attempt to breathe incident an endotracheal tube 52 will be transmitted through conduit 118 through patient supply conduit 46, filter 50, and be experienced through conduit 89 by the thermistor sensing probe 100. With reference now back to FIG. 3, a negative pressure applied through sensing tube 106 will allow diaphragm 108 to deflect rapidly upward to the limits of its travel in chamber 104 thus causing the volume of gas in that chamber to move very rapidly through sensing tube 106 and past thermistor 110, thus causing very rapid cooling of thermistor 110 and subsequent alteration of its resistance so as to derive an electrical signal. It has been determined that through the utilization of very flexible diaphragm materials and a very small cross-section sensing tube, the small volume of air making up the capacity of chamber 104 can be caused to move past the thermistor 110 at a very rapid rate, thus causing very rapid cooling and a subsequent rapid change in the resistance thereof. With reference to FIG. 1, it may be seen that this sudden change in electrical properties may be used to effect the operation of control circuit 90 and piston control device 64. It has been determined that thermistor sensing probes in the manner contemplated by the invention have had sensitivities of orders of magnitude greater than prior art sensing devices.

Figure 4:
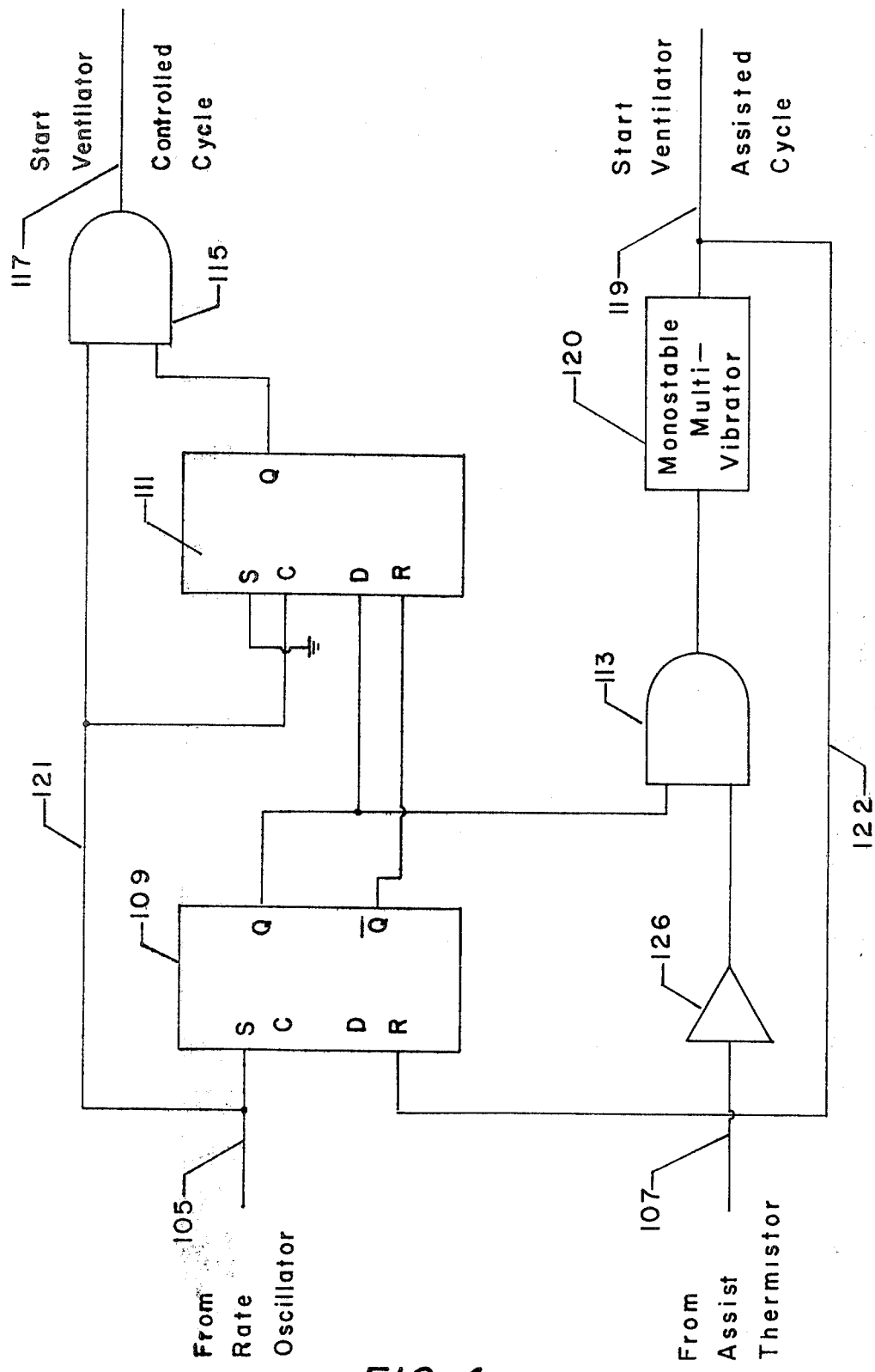
FIG. 4 is a logic diagram of a logic circuit such as might be utilized with Applicant's invention.

FIG. 4 is illustrative of a logic circuit in which the signal from the thermistor sensing probe 100 might be employed. As is commonly known in the art, a rate oscillator may be set to give an output pulse train at a desired breathing rate on a lead 105. The first such rate pulse received from the rate oscillator sets a first flip-flop 109, making its Q output high thus enabling first AND gate 113. Upon receipt of an electric signal from assist thermistor 110 on line 107, an inverter 126 may operate on and amplify that pulse and be transmitted to enabled AND gate 113, thereby supplying input signal to monostable multivibrator 120. The resultant signal from monostable multivibrator 120 would be supplied to system command lead 119 commanding the ventilator to start an assisted cycle. At the same time, system logic reset lead 122 causes reset of first flip-flop 109, thus disabling first AND gate 113 until a subsequent pulse is received on lead 105 from the system rate oscillator. It will be noted that the signal from the system rate oscillator is also incident upon a second flip-flop 111 of the D type (D for data) on a lead 121 and also this signal pulse enables a second AND gate 115. Whenever a signal is transmitted by way of this second flip-flop 111 so as to render its Q output high, a ventilator controlled cycle is started in response to an apneic condition of the patient. This part of the logic circuit is conventional and has been presented merely for completeness.

Thus there has been described a thermistor assist sensing invention that will provide much greater sensitivity than has been known by the prior art. It has been demonstrated that the reliability, maintainability, and ease of operation have been highly enhanced through the novel advantages of the invention.

It is here pointed out that although the present invention has been shown and described with reference to particular embodiment, nevertheless various changes and modifications obvious to one skilled in the art to which the invention pertains are deemed to lie within the purview of the invention.

What is claimed and desired to be secured by Letters Patent of the United States is:

1. In a respiratory ventilator of the type having means for providing a constant reference respiratory pressure and means for providing a respiration assist mode for a patient, an improved sensor for actuating said assist mode providing means, comprising:
   a housing having a chamber, said chamber being divided into first and second compartments;
   first conduit means in said housing having an elongated reduced diameter tubular passage for fluidly communicating a patient-induced pressure to said first compartment;
   second conduit means in said housing for fluidly communicating said reference pressure to said second compartment;
   diaphragm means, in said chamber, for (a) dividing said chamber into said first and second compartments, and (b) providing a high velocity, low volume flow of gas through said first conduit means in response to a patient-induced pressure differential between said first and second compartments, the velocity and volume of said flow of gas being determined at least substantially in part by the diameter of said passage;
   fluid flow sensing means in said first conduit means for producing an electrical output signal in response to said flow of gas through said first conduit means; and
   actuation means, responsive to said electrical output signal, for actuating said assist mode providing means.

2. The sensor of claim 1, wherein said fluid flow sensing means produces said electrical output signal in response to a change in temperature induced by said flow of gas.

3. The sensor of claim 2, wherein said fluid flow sensing means includes a thermistor.

4. The sensor of claim 1, wherein said diaphragm means has sufficient sensitivity to provide said flow of gas in response to a slight pressure differential between said first and second compartments induced by the initiation of inhalation by said patient.

5. The sensor of claim 1, wherein the volume and velocity of said flow of gas are functions of the respective dimensions of said chamber and said first conduit means.

6. The sensor of claim 1, wherein said actuation means comprises:
   oscillator means for generating a breathing rate signal;
   first switching means actuated in response to said breathing rate signal, for producing a first intermediate signal;
   gating means, receiving said first intermediate signal and said output signal from said sensing means, for producing a second intermediate signal in response to the reception of said first intermediate signal and said output signal;
   means for generating a command signal in response to said second intermediate signal; and
   second switching means for actuating said assist mode providing means in response to said command signal.

7. The sensor of claim 6, wherein said actuation means further comprises:
   means for de-actuating said first switching means in response to said command signal to enable a re-actuation of said first switching means in response to a subsequent breathing rate signal.

8. In a respiratory ventilator of the type having means for providing a constant respiratory reference pressure and means for providing assist mode respiration for a patient, an improved mechanism for actuating said assist mode providing means, comprising;
   a breathing gas supply conduit in fluid communication with the breathing passages of said patient;
   breathing gas delivery means for conducting breathing gas to said patient through said breathing gas supply conduit in response to the actuation of said assist mode providing means;
   a chamber having first and second conduits, said first conduit being in fluid communication with said breathing gas supply conduit, said first conduit having an elongated restricted diameter passageway therethrough and subject to a variable, patient-induced pressure from said breathing gas supply conduit, said second conduit being subject to said constant reference pressure;
   pressure-sensitive means in said chamber for providing a high-velocity, low volume flow of gas through said first conduit in response to a pressure differential between said first and second conduits, the velocity and volume of said flow of gas being determined at least substantially in part by the restricted diameter of said passageway;
   temperature-sensitive means in said first conduit for producing an electrical output signal in response to temperature changes induced by said flow of gas; and
   actuation means responsive to said output signal, for actuating said assist mode providing means.

9. The mechanism of claim 8, wherein said pressure-sensitive means comprises a resilient diaphragm dividing said chamber into first and second compartments, said first compartment in fluid communication with said first conduit and said second compartment in fluid communication with said second conduit.

10. The mechanism of claim 9, wherein said diaphragm is of sufficient sensitivity to provide said flow of gas in response to a predetermined pressure differential between said first and second conduits induced by the initiation of a respiratory cycle by said patient.

11. The mechanism of claim 8, wherein said temperature-sensitive means comprises a thermistor.

12. The mechanism of claim 8, wherein said actuation means comprises:
   first switching means for producing a first pulse in response to a breathing rate signal;
   gating means responsive to said output signal from said temperature-responsive means and to said first pulse to produce a second pulse;
   means for generating a command signal in response to said second pulse;
   second switching means for actuating said assist mode providing means in response to said command signal; and
   resetting means for de-actuating said first switching means in response to said command signal to enable a re-actuation of said first switching means in response to a subsequent breathing rate signal.

* * * * *